United States Patent

Sheridan et al.

[11] Patent Number: 6,008,396
[45] Date of Patent: Dec. 28, 1999

[54] HOT OIL PROCESS FOR PRODUCING ISOCYANATO ORGANOSILANES

[75] Inventors: Robert E. Sheridan, Marietta, Ohio; Kenneth W. Hartman, Middlebourne, W. Va.

[73] Assignee: OSI Specialties, Inc., Greenwich, Conn.

[21] Appl. No.: 09/039,052

[22] Filed: Mar. 13, 1998

Related U.S. Application Data

[60] Provisional application No. 60/043,660, Apr. 11, 1997.

[51] Int. Cl.$^6$ ...................................................... C07F 7/10
[52] U.S. Cl. .............................................................. 556/414
[58] Field of Search ............................................... 556/414

[56] References Cited

U.S. PATENT DOCUMENTS

| | | |
|---|---|---|
| 3,494,951 | 2/1970 | Berger ...................................... 556/414 |
| 3,598,852 | 8/1971 | Berger ...................................... 556/414 |
| 3,607,901 | 9/1971 | Berger . | 
| 3,642,854 | 2/1972 | Kozjukov . |
| 4,064,151 | 12/1977 | Hedaya et al. ........................... 556/414 |
| 4,654,428 | 3/1987 | Kurashima et al. . |
| 4,873,365 | 10/1989 | Luh et al. . |
| 5,218,133 | 6/1993 | Pepe . |
| 5,393,910 | 2/1995 | Mui et al. ................................. 556/414 |

FOREIGN PATENT DOCUMENTS

| | | |
|---|---|---|
| 0266661 | 4/1994 | European Pat. Off. . |
| 0795544 | 3/1997 | European Pat. Off. . |
| 57218101 | 6/1984 | Japan . |
| 9232697 | 11/1993 | Japan . |
| 91351230 | 12/1993 | Japan . |
| 92302407 | 6/1994 | Japan . |
| 1486 | 1/1998 | Japan . |
| 9757709 | 1/1998 | Japan . |

*Primary Examiner*—Paul F. Shaver
*Attorney, Agent, or Firm*—Edward K. Welch; Timothy X. Witkowski; Andrew S. Reiskind

[57] ABSTRACT

Disclosed is a process for making isocyanatoorganosilane by adding a carbamatoorganosilane of the general formula to an inert liquid medium and holding the mixture thus formed at a temperature and pressure effective to convert said carbamatoorganosilane to isocyanatoorganosilane.

10 Claims, No Drawings though the use of pre-stripped liquid media is not necessary. Some additional light ends may be formed under reaction conditions by decomposition of the liquid medium or impurities it may contain. These light ends may also co-distill with the desired isocyanatoorganosilane. In most cases these light boiling contaminants can be separated from the isocyanatoorganosilane by simple distillation with a relatively small number of plates.

HOT OIL PROCESS FOR PRODUCING ISOCYANATO ORGANOSILANES

This application is a continuation of provisional application 60/043,660 filed Apr. 22, 1997.

BACKGROUND OF THE INVENTION

There has been a continuing need for an economical method of preparing isocyanatoorganosilanes, including isocyanatoalkylsilanes, in high yields and purities from relatively non-hazardous raw materials. Heretofore, isocyanatoorganosilanes have been made in relatively low volumes by inefficient or costly processes.

For example, isocyanatoorganosilanes have been prepared by processes involving the addition of hydrosilanes to unsaturated isocyanates, particularly allyl isocyanate, in the presence of a noble metal catalyst. Allyl isocyanate is a highly toxic raw material of limited commercial availability.

Processes also are known wherein isocyanatoalkylsilanes are prepared from carbamatoalkylsilanes at low temperature in the liquid phase, or from aminoalkylsilanes and highly toxic phosgene by various routes. All liquid phase processes disclosed thus far suffer from one or more disadvantages of low yield, slow kinetics, need for highly toxic raw materials, need for extensive work-up or purification, often in the presence of higher levels of close-boiling contaminants, and substantial generation of by-products and waste materials.

High temperature, vapor phase processes are also known; but these generally require specialized equipment capable of high temperature operation, with concurrent extensive capital investment. A method for making 2-isocyanatoethoxysilanes by liquid phase thermal rearrangement of N-silyl-2-oxazolidinones has also been disclosed. The bonding of the isocyanatoalkyl groups to silicon atoms in these molecules is through hydrolyzable silicon-oxygen bonds, and the silane moiety does not contain additional alkoxy groups as are present and often necessary in current commercially useful isocyanatoalkylsilanes.

BRIEF SUMMARY OF THE INVENTION

The present invention provides a method of preparing isocyanatosilanes by the addition of a carbamatoorganosilane to an inert liquid medium at elevated temperatures and reduced pressures effective to decompose the carbamatoorganosilane to the corresponding isocyanatoorganosilane. Isocyanatoorganosilanes that can be prepared include those of the formula $R_x(R'O)_{3-x}SiR"NCO$ (I) wherein x is 0, 1, 2, or 3, each R separately represents a hydrocarbon of 1 to 15 carbon atoms, each R' is separately R, a silyl group $R_3Si$—, or a siloxy group $R_3Si(OSiR_2)_m$— wherein m is 1 to 4, or when x is 0 or 1 two R' groups together may form a divalent siloxy group —$R_2(OSiR_2)_n$— wherein n is 3 to 5 thus forming a cyclic siloxane, R" represents a divalent hydrocarbon group of 1 to 20 carbon atoms, wherein R, R' and R" may also contain heteroatom functional groups such as ether, thioether, sulfone, ketone, ester, amide, nitrile, or halogen.

DETAILED DESCRIPTION OF THE INVENTION

Adding carbamatosilanes to a hot, inert liquid medium, yields isocyanatoorganosilanes in high yields and purities with no need to use reaction aids, such as highly toxic phosgene or allyl isocyanate, with no generation of highly corrosive hydrogen chloride as a by-product and with minimal formation of other by-products, contaminants, and waste materials. Because the method can be operated continuously with short residence times, a relatively small reactor is capable of large throughputs with a correspondingly small capital investment.

The method of the present invention also can provide isocyanatoorganosilanes in which the isocyanate groups are attached to silicon atoms through branched hydrocarbon groups (R"). Such compounds have isocyanate groups with varying degrees of reactivity, which provide corresponding desirable variations in the performance properties of products incorporating said isocyanatoorganosilanes, including wet strengh, flexibility, and oxidation resistance.

The method of the present invention also can provide isocyanatoorganosilanes wherein the silicon atom bearing the isocyanatoorgano group is further substituted by siloxy groups. These compounds combine the high surface activity of low molecular weight siloxanes with the high reactivity of the isocyanate group, and are useful in providing improved coatings, particularly for metallic substrates such as automobiles.

The liquid reaction medium must be inert, i.e., it is chemically stable in the absence of oxygen at the temperature and pressure at which the reaction is carried out, it exhibits a boiling point higher than that of the isocyanatoorganosilane and it does not boil at the temperature and pressure at which the reaction described herein is carried out. In addition, the liquid medium must either be inert to the reactant carbamatoorganosilane and the product isocyanatoorganosilane, or be rendered inert to the reactant and product by reaction of the liquid medium with the carbamatoorganosilane or the isocyanatoorganosilane. By "rendered inert" is meant that the liquid medium can react with, for instance, the reactant carbamatoorganosilane, such that the liquid medium is converted into another product which functions as a satisfactory inert liquid medium for the reaction described herein. Such reaction consumes only a small portion of the carbamatoorganosilane, given the relatively high ratio of the liquid medium to the reactant.

The liquid medium can be any organic liquid satisfying these conditions, such as hydrocarbons and mixtures of hydrocarbons, unsubstituted or substituted, and optionally containing oxygen or other hetero atoms. Examples include linear and branched alkanes, esters, ethers, cycloaliphatic and aromatic hydrocarbons, fluorocarbons, fluorocarbon ethers, and silicone fluids. Specific examples are HE-200 Vacuum Pump Oil, stripped DARADINE® 68 refined petroleum oil, MULTITHERM® IG-2 refined paraffinic distillate, KRYTOX 107 perfluoropolyether, CHEMTHERM® 700 isomeric dibenzyl toluenes, and SYLTHERM® 800 polysiloxane. Particularly useful are the heat transfer fluids which are commercially available through various sources.

An example of a liquid medium which can be rendered unreactive under the reaction conditions would be a hydroxy terminated polyether. Under the reaction conditions a hydroxyl group would react with either the isocyanate or the alkoxysilicon functionality. In either case the reaction will result in an endcapped polyether which is inert to further reaction.

Many of the liquid media described are available as mixtures of isomers or with a distribution of molecular weights. Some portion of the liquid medium may distill under the reaction conditions. The light ends of these compounds may be allowed to co-distill with the desired isocyanatoorganosilane which is further refined at a later date if needed, or the liquid medium can be pre-stripped of their lower boiling components before use.

The method of the present invention involves the thermal decomposition in the liquid phase, generally at ambient or reduced pressure, of carbamatoorganosilane of the general formula $$R_x(R'O)_{3-x}SiR''NHCO_2R \quad (II)$$

wherein R, R', R", and x are as defined above. While the R and R' groups may vary within the product isocyanatoorganosilane or starting carbamatoorganosilane molecules, the R and R' groups attached to the oxygen atoms in the isocyanatoalkylsilanes will generally, but not necessarily, be the same.

Preferably R is a lower alkyl of 1 to 4 carbon atoms, but may also be isopropyl or t-butyl to provide for slower hydrolyzation of the silane. Preferably R' is an alkyl group or halogenated alkyl group of 1 to 12 carbon atoms, a cycloalkyl group or halogenated cycloalkyl group of 5 to 8 carbons, an aryl group of 6 to 14 carbons, or an alkaryl or aralkyl group of 7 to 15 carbons. More specifically R' is a lower alkyl of 1 to 4 carbon atoms, or a branched alkyl of 3 to 5 carbon atoms. R" preferably is a linear or branched divalent saturated or unsaturated hydrocarbon group of 1 to 20 carbon atoms attached to silicon by a silicon-carbon bond, including linear and branched alkylene, arylene, alkarylene, and aralkylene groups. Specific examples of R" are $(CH_2)_m$ wherein m=1 to 20, propylene, butylene and phenyl-butylene.

Thus, the method is represented by the following general equation:

$$R_x(R'O)_{3-x}SiR''NHCO_2R \xrightarrow{\text{Inert Solvent/Heat}} R_x(R'O)_{3-x}SiR''NCO + ROH$$

wherein R, R', R", and x are defined as above.

Preferably the reaction is conducted at an elevated temperature between 200° to 400° C., more preferably 250° to 350° C. The pressure of reaction should be at about 10 to about 200 mm Hg, but preferably the pressure is between 30 to 150 mm Hg.

The carbamate silane is added to the solvent wherein the solvent is hot enough to convert the carbamate to the isocyanate. Thus, the amount of carbamate to solvent at any time is small (<5 wt-%) because as soon as the carbamate touches the solvent it will convert to the isocyanate. Thus, as long as there is an excess of solvent, (e.g.,>85% by volume), then this will occur. The carbamate and solvent preferably should not be combined and then heated.

The method of the present invention can be run in a semi-continuous fashion in any flow through apparatus having the capacity for maintaining an inert atmosphere or a reduced pressure, for maintaining a liquid level, and having the capacity to heat the liquid to the desired temperature range, the ability to feed the carbamatoorganosilane into the heated liquid, for removing the ROH byproduct, a column for rectification of the product, if needed, and condensing the desired isocyanatoorganosilane. Said types of apparatus with various capacities are readily available within the chemical industry and can be operated without additional capital expense.

Preferably there is a distillation column attached to the reactor such that the volatile isocyanate silane comes off the reaction system, and unreacted carbamate silane, if any, is returned to the reaction system. Moreover, the alcohol produced in this reaction should be flashed off the product and through the condenser.

Under optimal conditions, the method of the present invention provides isocyanatoorganosilane products requiring no further purification for industrial use. Where an impurity is present, the impurity is either a component of the liquid medium or the starting carbamatoorganosilane, which can typically be removed by simple distillation and recycled if desired.

The starting carbamate silanes may be made as is known in the art. For example, from an amino silane and chloroformate, from a dialkylcarbonate and an amino silane or from a chloroalkyl silane and sodium cyanate in the presence of an alcohol.

The products of the method of the present invention, namely isocyanatoorganosilanes, and particularly $(MeO)_3Si(CH_2)_3NCO$ and $(EtO)_3Si(CH_2)_3NCO$, with numerous uses in manufacturing industries. One use, for example, is in the preparation of silane-grafted polymers as disclosed in U. S. Pat. Nos. 4,113,691 and 4,146,585.

EXAMPLES

Example 1

Production of gamma-isocyanatopropyltrimethoxysilane from methyl carbamatopropyltrimethoxysilane.

To a 4-neck 1 liter round bottom flask fitted with a 10 plate Oldershaw column and a distillation head, a thermometer, and magnetic stir bar were charged 201 grams of HE-200 Vacuum Pump Oil (Leybold Vacuum Products, Inc., Export, Pa.), which is a refined petroleum oil. The oil was heated to a temperature of 315° C. and the system's pressure reduced to 70 mmHg. The condenser coolant temperature was set at 50° C. Methyl carbamatopropyltrimethoxysilane was pumped into the reactor at a rate of 1.26 to 2.61 grams per minute. A short time after the feed was started the head temperature rose to approximately 134° C. and product take off started using a 1:1 reflux ratio. These conditions were maintained until 282 grams of the carbamnate had been fed. A toal of 225 grams of product were collected overhead having an average purity of 98.6% gamma-isocyanatopropyltrimethoxysilane (93.2% reaction yield) as determined by gas chromatographic analysis.

Example 2

Production of gamma-isocyanatopropyltriethoxysilane from ethyl carbamatopropyltriethoxysilane.

This reaction was run as per Example 1, but with the following changes:

The reaction flask was charged with 206 grams of stripped DARADINE® 68 (Dryden Oil Co.) a refined petroleum oil used as a vacuum pump oil) and heated to 340° C. and the system pressure set to 38 mmHg. The starting carbamate, ethyl carbamatopropyltriethoxysilane was fed at a rate of approximately 1.0 grams per minute and product collected overhead using a 4:1 reflux ratio at a head temperature of 144° C. A total of 349 grams of carbamate were fed into the system and 254.4 grams of product was collected having an average purity of 96.6% (83.5% reaction yield) as determined by gas chromatographic analysis.

Example 3

Use of paraffinic distillate as the inert solvent:

The experiment was run as described in Example 1 with the following changes and results:

A total of 92.6 grams of methyl carbamatopropyltrimethoxysilane was fed at a feed rate of 0.86 grams per minute into 201 grams of MULTITHERM IG-2® (Multitherm Corp., Colwyn, Pa.) refined paraffinic distillate. The pot temperature was maintained at 300–305° C. and the pressure set to 70–75 mmHg. A total of 64.0 grams of product was recovered overhead having an average purity of 96.7% isocyanatopropyltrimethoxysilane (79.9% reaction yield) as determined by gas chromatographic analysis.

Example 4

Use of aromatic hydrocarbon as the inert solvent:

The experiment was run as described in Example 1 with the following changes and results:

A total of 90 grams of methyl carbamatopropyltrimethoxysilane was fed at a feed rate of 1.0 grams per minute into 200 grams of CHEMTHERM 700® (Coastal Chemical Co., Inc., Houston, Tex.) aromatic hydrocarbon containing isomers of dibenzyltoluene. The pot temperature was maintained at 300° C. and the pressure set to 100 mmHg. A total of 90 grams of product was recovered overhead having an average purity of 89.0% isocyanatopropyltrimethoxysilane (90.2% reaction yield) as determined by gas chromatographic analysis.

Example 5

Use of perfluoropolyether as an inert solvent.

The experiment was run as described in Example 1 with the following changes and results:

A total of 152.4 grams of methyl carbamatopropyltrimethoxysilane was fed at a feed rate of 0.5 grams per minute into 202 grams of KRYTOX 107® (E. I. DuPont de Nemours and Co., Wilmington, Del.) perfluoropolyether. The pot temperature was maintained at 342–355° C. and the pressure set to 70 mmHg. A total of 121.8 grams of product was recovered overhead having an average purity of 93.7% isocyanatopropyltrimethoxysilane (86.6% reaction yield) as determined by gas chromatographic analysis.

Example 6

Use of polydimethylsiloxane as the inert solvent:

The experiment was run as described in Example 1 with the following changes and results:

A total of 114 grams of methyl carbamatopropyltrimethoxysilane was fed at a feed rate of 0.5 grams per minute into 200 grams of SYLTHERM 800® (Dow Chemical Co., Midland Mich.), polydimethylsiloxane. The pot temperature was maintained at 295-300° C. and the pressure set to 78 mmHg. A total of 89.4 grams of product was recovered overhead having an average purity of 77.6% isocyanatopropyltrimethoxysilane (70.3% reaction yield) as determined by gas chromatographic analysis.

Example 7

Larger Scale Preparation of gamma-isocyanatopropyltrimethoxysilane from methyl carbamatopropyltrimethoxysilane using MULTITHERM® IG-2 as the inert solvent:

The apparatus consisted of a 200 liter glass kettle, seated in a 4 zone electric heating mantle. The top of the kettle was insulated. A 6 feet×6 inch (182.9 cm×15.2 cm) insulated column was packed with 6 feet (182.9 cm)of Hastelloy packing to make 12–15 theoretical trays. A condenser was at the top of the column with a return to the kettle as well as to one of two 25 liter receiver pots. Tempered water at 60–80° C. was used in the condenser. The kettle contained a glass agitator with 4 blades that were 1.5 inches (3.8 cm) thick & 5 inches (12.7 cm) from tip to tip. An oil driven pump provided the vacuum. Vacuum was measured in the kettle head space.

192 Pounds (71.6 Kg) of MULTITHERM IG-2 were added to the kettle through the heat exchanger to reach a temperature of 120° C. upon entry into the kettle. The oil was heated to 300° C. and the pressure reduced to 70 mmHg. Methyl carbamatopropyltrimethoxysilane was pumped into the oil at an initial rate of 5 pounds/hr (1.9 Kg/hr). During this reaction, the feed rates were varied between 5–10 pounds/hr (1.9–3.7 Kg/hr) with an average feed rate of 5.10 pounds/hr (1.9 Kg/hr). A total of 344 pounds (128.3 Kg) of the carbamate were fed over the 72 hour reaction period yielding gamma-isocyanatopropyltrimethoxysilane with purities on the average >96%.

Example 8

Larger Scale Preparation of gamma-isocyanatopropyltrimethoxysilane from methyl carbamatopropyltrimethoxysilane using recycled Multitherm® IG-2 as the inert solvent:

Multitherm IG-2 previously used to prepare gamma-Isocyanatopropyltrimethoxysilane from methyl carbamatopropyltrimethoxysilane was filtered. 192 Pounds (71.6 Kg) of this recycled oil were added to the apparatus mentioned in example 7. During this reaction, the feed rates were varied between 2.5–5.5 pounds/hr (0.9–2.0 Kg/hr) with an average feed rate of 3.33 pounds/hr (1.2 Kg/hr). A total of 193 pounds (72.0 Kg)of the carbamate were fed over the 71 hour reaction period yielding gamma-isocyanatopropyltrimethoxysilane with purities >96% and on the average >97.5%.

Example 9

Larger Scale Preparation of gamma-isocyanatopropyltriethoxysilane from ethyl carbamatopropyltriethoxysilane using Multitherm® IG-2 as the inert solvent:

This example was similar to example 7 with the exception that ethyl carbamatopropyltriethoxysilane was used as the feed. During this reaction, the feed rates were varied between 1.3–3.6 pounds/hr (0.5–1.3 Kg/hr) with an average feed rate of 3.6 pounds/hr (1.3 kg/hr). A total of 197 pounds (73.5 Kg) of the carbamate were fed over the 55 hour reaction period with purities of gamma-isocyanatopropyltriethoxysilane initially >98% but falling to 90% after 37 hours due to the build up of an impurity.

Comparison with Liquid Phase Cracking in the absence of hot, inert liquid medium:

In a 1 liter 3-neck, round bottomed flask equipped with a 10 plate Oldershaw distillation column, distillation head, and receiver, thermometer, and magnetic stir bar was placed 349.6 grams of methyl carbamatopropyltrimethoxysilane. The pot contents were heated to between 190–204° C. at 52–54 mmHg pressure for a total of 7 hours. During this time a total of 205.3 grams of product was collected overhead in several distillate cuts, having an average purity of 93.1% isocyanatopropyltrimethoxysilane giving the reaction a net yield of 67.3%. The reactor contained 96.9 grams of heavies and the net material balance 96.4%.

Similar liquid phase results were obtained with ethyl carbamatopropyltriethoxysilane as reported in Example A of U.S. Pat. No. 5,393,910, granted to the assignee of the present invention.

What is claimed is:

1. A method comprising adding a carbamatoorganosilane to an inert liquid medium which is at a temperature and pressure effective to convert said carbamatoorganosilane to an isocyanatoorganosilane.

2. A method according to claim 1 additionally comprising isolating the isocyanatoorganosilane formed.

3. A method according to claim 1 wherein the isocyanatoorganosilane is of the formula

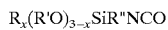
$R_x(R'O)_{3-x}SiR''NCO$ wherein x is an integer having a value of 0, 1, 2, or 3, each R separately represents an alkyl group or halogenated alkyl group of 1 to 12 carbon atoms, a cycloalkyl group or halogenated cycloalkyl group of 5 to 8 carbons, an aryl group of 6 to 14 carbons, or an alkaryl or aralkyl group of 7 to 15 carbons, each R' is separately R or a silyl group $R_3Si$—, or a siloxy group $R_3Si(OSiR_2)_m$— wherein m is an integer having a value of 1 to 4, or when x is 0 or 1 two R' groups taken together may form a divalent siloxy group —$R_2(OSiR_2)_n$— wherein n is an integer having a value of 3, 4, or 5 thus forming a cyclic siloxane with the silicon atom bearing the isocyanatoorgano group, R'' represents a linear or branched divalent saturated or unsaturated hydrocarbon group of 1 to 20 carbons attached to silicon by a silicon-carbon bond; and wherein R, R', and R'' optionally may contain heteroatom functional groups such as ether, thioether, sulfone, ketone, ester, amide, nitrile, or halogen.

4. A method according to claim 1 wherein the carbamatoorganosilane is of the formula

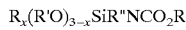
$R_x(R'O)_{3-x}SiR''NCO_2R$ wherein x is an integer having a value of 0, 1, or 2, each R separately represents an alkyl group or halogenated alkyl group of 1 to 12 carbon atoms, a cycloalkyl group or halogenated cycloalkyl group of 5 to 8 carbons, an aryl group of 6 to 14 carbons, or an alkaryl or aralkyl group of 7 to 15 carbons, each R' is separately R or a silyl group $R_3Si$—, or a siloxy group $R_3Si(OSiR_2)_m$— wherein m is an integer having a value of 1 to 4, or when x is 0 or 1 two R' groups taken together may form a divalent siloxy group —$R_2(OSiR_2)_n$— wherein n is an integer having a value of 3, 4, or 5 thus forming a cyclic siloxane with the silicon atom bearing the isocyanatoorgano group, R'' represents a linear or branched divalent saturated or unsaturated hydrocarbon group of 1 to 20 carbons attached to silicon by a silicon-carbon bond, wherein R, R', and R'' may also contain heteroatom functional groups such as ether, thioether, sulfone, ketone, ester, amide, nitrile, or halogen.

5. A process according to claim 1 wherein the liquid medium is a hydrocarbon.

6. A process according to claim 1 wherein the liquid medium is selected from the group coonsisting of vacuum pump oil, stripped refined petroleum oil, refined paraffinic distillate, pefluoropolyether, isomeric dibenzyl toluenes, and polysiloxane.

7. A process according to claim 1 wherein the liquid medium is at a temperature between about 200° and about 400° C.

8. A process according to claim 1 wherein the pressure is between about 10 to about 200 mm Hg.

9. A process according to claim 1 wherein the isocyanatoorganosilane is selected from the group of isocyanatopropyltrimethoxysilane and isocyanatopropyltriethoxysilane.

10. A process according to claim 4 wherein x has a value of 0, 1, or 2, R and R' are selected from the group of methyl and ethyl groups, and R'' is a linear propylene group.

* * * * *